United States Patent [19]

Dattani et al.

[11] Patent Number: 5,200,431
[45] Date of Patent: Apr. 6, 1993

[54] PROCESS FOR THE SEPARATION OF HALOGENATED HYDROCARBONS BY EXTRACTIVE DISTILLATION

[75] Inventors: Pravin K. Dattani, Hockessin, Del.; John D. Scott, Cheshire, England; Barry W. Farrant, Lancashire, England; Charles J. Shields, Cheshire, England

[73] Assignee: Imperial Chemical Industries PLC, London, England

[21] Appl. No.: 747,755

[22] Filed: Aug. 21, 1991

[30] Foreign Application Priority Data

Aug. 21, 1990 [GB] United Kingdom ............... 9018372

[51] Int. Cl.$^5$ ............................................. C07C 17/38
[52] U.S. Cl. ...................................... 570/178; 203/64
[58] Field of Search ........................... 570/178; 203/64

[56] References Cited

U.S. PATENT DOCUMENTS

| | | | |
|---|---|---|---|
| 3,689,374 | 9/1972 | Hanson | 570/178 |
| 3,819,493 | 6/1974 | Fozzard | 570/178 |

*Primary Examiner*—Marianne M. Cintins
*Assistant Examiner*—John D. Peabody, III
*Attorney, Agent, or Firm*—Cushman, Darby & Cushman

[57] ABSTRACT

Method for separating 1,1,1,2-tetrafluoroethane from a mixture thereof with chlorine-containing halogenated hydrocarbons such as HCFC's 1122, 124, 114, 114a and 133a which comprises adding an extraction agent to the mixture and extractively distilling the mixture in an extractive distillation zone from which HFA 134a containing less than 10 ppm of chlorinated contaminants is recovered. Suitable extraction agents include trichloroethylene, perchloroethylene, alpha-pinene and cyclohexane.

10 Claims, 1 Drawing Sheet

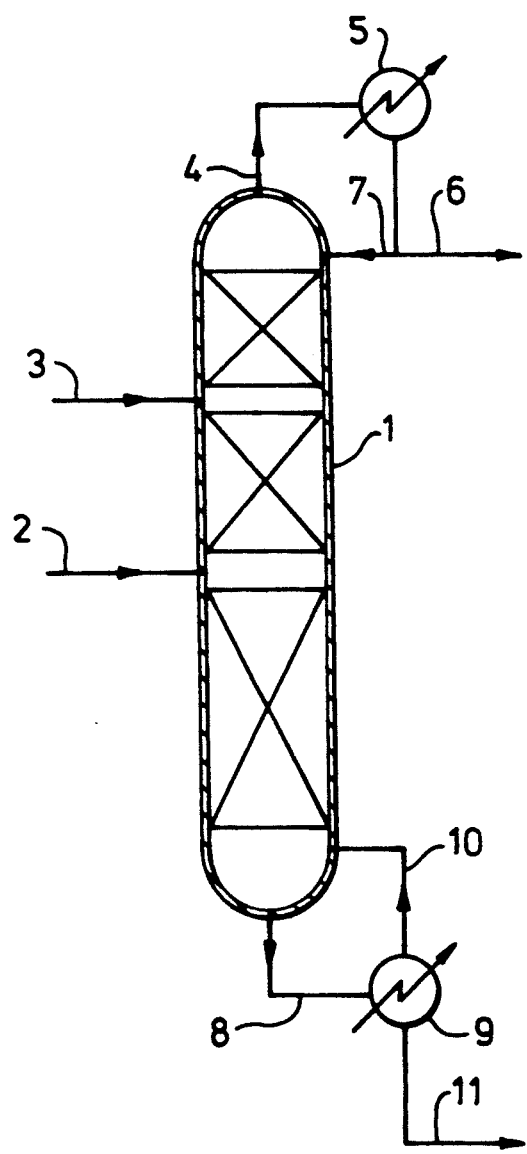

PROCESS FOR THE SEPARATION OF HALOGENATED HYDROCARBONS BY EXTRACTIVE DISTILLATION

This invention relates to a separation process and more particularly to a process for the separation of halogenated hydrocarbons by extractive distillation.

It is well known to react hydrogen fluoride with various $C_2$ compounds, for example trichloroethylene or 2-chloro-1,1,1-trifluoroethane or to hydrogenate chlorofluorocarbons, in order to make 1,1,1,2-tetrafluoroethane (HFA 134a) which is useful as a refrigerant. A typical product stream obtained in these processes can contain unchanged starting materials together with organic and inorganic by-products as well as the desired HFA 134a.

Various conventional separation techniques, for example distillation and aqueous scrubbing, have been proposed for the purpose of separating HFA 134a from other components of the product stream. Particular difficulty can be experienced in removing other halogenated hydrocarbons containing chlorine, especially those having boiling points close to that of HFA 134a. One of these is 2-chloro-1,1-difluoroethylene (HCFC 1122) which, although present in relatively small amounts, must be removed because of its toxicity.

Several methods have been proposed for substantially reducing the HCFC 1122 content of HFA 134a. Thus, U.S. Pat. No. 4,129,603 describes a method involving contacting the impure HFA 134a with an aqueous solution of a metal permanganate. In the process described in U.S. Pat. No. 4,158,675, the impure HFA 134a obtained by fluorinating 2-chloro-1,1,1-trifluoroethane over a chromia catalyst is passed with hydrogen fluoride over a chromia catalyst at a much lower temperature than used in the manufacturing process. The purification process described in U.S. Pat. No. 4,906,796 comprises passing the impure HFA 134a over a zeolite having a mean pore size between 3.8 and 4.8 Angstroms.

It has now been found that HCFC 1122 can be removed from a mixture of HFA 134a and HCFC 1122 by a simple extractive distillation process which also removes other chlorinated species from the HFA 134a.

According to the present invention there is provided a method for separating 1,1,1,2-tetrafluoroethane from a mixture containing 1,1,1,2-tetrafluoroethane and chlorine-containing halogenated hydrocarbons which comprises adding an extraction agent to said mixture, extractively distilling the mixture in an extractive distillation zone and recovering 1,1,1,2-tetrafluoroethane from the extractive distillation zone, the extraction agent being selected from trichloroethylene, perchloroethylene, carbon tetrachloride and aliphatic hydrocarbons containing from 4 to 10 carbon atoms. Mixtures of extraction agents may be used, if desired.

The aliphatic hydrocarbon may be saturated or ethylenically unsaturated and it may be cyclic or acylic. The carbon atom chain of the acyclic hydrocarbon may be straight or branched but usually will be a straight chain. Examples of particularly suitable hydrocarbons are hexane, cyclohexane and alpha-pinene. Good separation of HCFC 1122 from HFA 134a has been achieved using trichloroethylene and alpha-pinene. Alpha-pinene is a bicyclic alkene containing 10 carbon atoms.

The extraction agents used in the method according to the invention are selected on the basis of their ability to extract a relatively large proportion of chlorinated species compared to HFA 134a from the mixtures being treated.

The method of the invention is broadly applicable to any mixture of HFA 134a and chlorine-containing halogenated hydrocarbons such as HCFC 1122 but is especially applicable to mixtures obtained in processes for the manufacture of HFA 134a by the reaction of hydrogen fluoride with $C_2$ compounds such as trichloroethylene and/or 1-chloro-2,2,2-trifluoroethane. The mixtures produced in such processes commonly contain major proportions of 1-chloro-2,2,2-trifluoroethane, 1,1,2,2-tetrafluoroethane (HFA 134) and hydrogen fluoride and minor proportions of other haloethanes and possibly HCFC 1122. The mixtures may also be obtained by hydrogenation of halocarbons such as 1-chloro-1,2,2,2-tetrafluoroethane (HCFC 124) and 1,1-dichloro-1,2,2,2-tetrafluoroethane (CFC 114a), such mixtures commonly containing major proportions of HCFC 124 and/or HCFC 114a. Treatment of mixtures containing HFA 134a and HFA 134 does not result in appreciable separation of these two components.

The HCFC 1122 or other chlorinated species content of mixtures treated in accordance with the invention is typically from 20 to 5000 ppm on a weight basis but mixtures containing smaller or larger amounts of HCFC 1122 or other chlorinated species may also be separated. If desired, the reaction stream may be given a pre-treatment in order to effect partial or essentially complete removal of HCFC 1122, one or more other chlorinated constituents and/or hydrogen fluoride before performing the separation method of the invention.

The method of the invention may be performed using conventional extractive distillation procedures. Thus, in a typical operation, a mixture containing HFA 134a and HCFC 1122 and/or other chlorinated species obtained as a reaction product in an HFA 134a production process is fed to the centre of a fractionating column whilst an extraction agent such as trichloroethylene, α-pinene, perchloroethylene or cyclohexane is fed to the upper part of the column. As distillation proceeds, the column provides an overheads fraction comprising HFA 134a containing less than 10 ppm by weight of HCFC 1122 and/or other chlorinated species and a bottoms fraction comprising the extraction agent and HCFC 1122 and/or other chlorinated species.

The column is suitably operated at a pressure of from 1 to 15 bars.

Trichloroethylene is a preferred extractant for use in the method of the invention because the bottoms fraction from the fractionation column comprising trichloroethylene and HCFC 1122 and/or other chlorinated species can be recycled to the fluorination reactor.

Use of perchloroethylene or carbon tetrachloride as extraction agent also provides a bottoms fraction which can be used directly as or as part of the feedstock for production of halogenated hydrocarbons. When α-pinene or another hydrocarbon is used as the extraction agent, it can be separated from the HCFC 1122 or other chlorinated species by a conventional fractional distillation for return to the extractive distillation column.

The invention will now be illustrated by reference to the accompanying drawing, the single FIGURE being a simplified flow diagram for the separation of HFA 134a (1,1,1,2-tetrafluoroethane) from a mixture thereof with HCFC 1122 (2-chloro-1,1-difluoroethylene) and/or other chlorinated species. For simplicity the invention is described in respect of separating HFA 134a from HCFC 1122 using trichloroethylene as extraction agent.

Referring to the FIGURE, a distillation column 1 is provided with a feed line 2 to the centre of the column and a feed line 3 to the upper part of the column. An overheads flow line 4 leads from the top of the column 1 to a condenser 5. A product flow line 6 leads from the condenser 5 with a reflux flow line 7 leading from the product flow line 6 back to the top of the column 1. A bottoms flow line 8 leads from the bottom of the column 1 to a reboiler 9 with a vapour return line 10 leading from the top of the reboiler back to the bottom of the column. A flow line 11 leads from the reboiler 9.

In operation, a mixture containing HFA 134a and 30 ppm HCFC 1122 obtained from a fluorination reactor (not shown) is fed via line 2 to the column 1 which is maintained at a pressure of from 1 to 15 bars. Trichloroethylene is fed to the column 1 via line 3. As distillation proceeds, an overheads fraction comprising HFA 134a containing less than 10 ppm of HCFC 1122 is taken from the top of the column 1 via flow line 4, condenser 5 and flow line 6. A bottoms fractions comprising trichloroethylene and HCFC 1122 is taken from the bottom of the column 1 via flow line 8, reboiler 9 and flow line 11 for recycling to the fluorination reactor.

The HFA 134a product obtained by the method of the invention may be subjected, as desired, to further purification procedures.

The extractive distillation may be used for separating HFA 134a from its mixtures with HCFC 1122 and/or haloethanes such as 2-chloro-1,1,1,2-tetrafluoroethane (HCFC 124), 2-chloro-1,1,1-trifluoroethane (HCFC 133a), 1,1-dichloro-1,2,2,2-tetrafluoroethane (CFC 114a) and/or 1,2-dichloro-1,1,2,2-tetrafluoroethane (CFC 114). The extractive distillation does not separate HFA 134a from HFA 134. Alpha-pinene is useful for separating HFA 134a from mixtures containing from 100 ppm to 5% of HCFC 124.

The invention is further illustrated by the following Examples.

EXAMPLE 1

A three neck round bottom flask was fitted with a gas sampling septum, stopper and tap (total vol 600 ml). The flask was evacuated then HCFC 1122 vapour (5 ml) and HFA 134a vapour (5 ml) were added through the septum. The flask was brought to atmospheric pressure by allowing air in through the tap. A vapour sample (20 ml) was withdrawn and analysed by gas chromatography to produce a reading of initial vapour composition. Air was then added to the flask (20 ml) followed by a sample of the relevant extraction agent or solvent (4 ml). The solvent was stirred for 45 minutes at 20° C. after which the head space was sampled (20 ml) and analysed by gas chromatography giving the final vapour composition. The corrected initial partial pressure ($P^*_I$), the final partial pressure ($P^*_F$) and the mass of gas dissolved in 4 ml of solvent were calculated.

Results for α-pinene as solvent were as follows:

|  | $P^*_I$ Atm × 10$^{-3}$ | $P^*_F$ Atm × 10$^{-3}$ | Mass Dissolved mg/4 ml | K | α |
|---|---|---|---|---|---|
| HCFC 1122 | 8.32 | 7.25 | 2.6 | 6.8 | |
| HFA 134a | 8.34 | 8.19 | 0.4 | 56.3 | 8.3 |

Results for trichloroethylene as solvent were as follows:

|  | $P^*_I$ Atm × 10$^{-3}$ | $P^*_F$ Atm × 10$^{-3}$ | Mass Dissolved mg/4 ml | K | α |
|---|---|---|---|---|---|
| HCFC 1122 | 7.95 | 7.04 | 2.3 | 13.2 | |
| HFA 134a | 7.71 | 7.48 | 0.6 | 54.5 | 4.1 |

K in the tables may be defined as mole fraction of material in vapour/mole fraction in liquid.

α in the tables = $K_{134a}/K_{1122}$

EXAMPLE 2

Three glass sample vials (volume 90 ml) were prepared and fitted with septa for gas addition and sampling. Each vial was evacuated, then filled to 1 atmosphere pressure with a previously prepared 1:1:1:1:1 gas mixture by volume of 134a, 134, 1122, 124 and 114x (an unresolved mixture of 114a and 114). A vapour sample (10 ml) was withdrawn from each sample vial and analysed by gas chromatography (gc) to obtain the initial gc area count for each component. The chosen extraction agent (10 ml) was then added to the vial and the contents were stirred for 1 hour at room temperature. A vapour sample (10 ml) was withdrawn, brought to atmospheric pressure by air addition, then analysed by gc to indicate the final gc area count for each component.

Table 1 lists the absolute drop in each component which occurred after exposure to the extraction agent (taken as an average of three runs). Table 2 shows the drop in components 134, 1122, 124 and 114x relative to that for 134a. This data is produced by normalising on the 134a, i.e. the 134a initial level is divided by 134a final level to produce a ratio with which all the final component levels are multiplied such that the 134a initial level divided by the normalised 134a final level equals 1.

TABLE 1

| Extraction Agent | Absolute Drop in component gc area count (%) | | | | |
|---|---|---|---|---|---|
|  | 134a | 134 | 1122 | 124 | 114x |
| Trichloroethylene | 49.8 | 55.9 | 83.2 | 75.8 | 84.2 |
| Tetrachloroethylene | 26.1 | 34.9 | 75.6 | 62.6 | — |
| Carbon tetrachloride | 36.4 | 43.8 | 79.5 | 70.6 | — |
| Hexane | 38.4 | 46.1 | 77.0 | 70.3 | 84.3 |
| Cyclohexane | 26.9 | 30.8 | 74.3 | 60.9 | 81.8 |
| α-Pinene | 46.0 | 45.0 | 79.0 | 70.2 | 82.1 |
| COMPARISON |  |  |  |  |  |
| 1,1,1-Trichloroethane | 63.9 | 67.1 | 85.4 | 82.3 | — |
| Pentachloroethane | 39.5 | 45.4 | 77.6 | 66.3 | 75.7 |
| Chloroform | 55.3 | 62.0 | 83.3 | 77.2 | — |
| 1,1,2-trichloro-1,2,2-trifluoroethane | 59.2 | 61.5 | 80.9 | 80.2 | — |
| Toluene | 61.9 | 72.1 | 84.7 | 85.3 | — |
| Ethanol | 71.7 | 83.4 | 81.8 | 90.8 | 78.2 |
| Methanol | 74.3 | 86.6 | 79.1 | 90.1 | 70.4 |
| Water | 7.5 | 12.4 | 7.1 | 5.1 | — |
| Triethylamine | 55.5 | 70.4 | 85.1 | 90.2 | 85.9 |
| Perfluorohexane | 49.9 | 52.4 | 63.4 | 67.5 | 80.1 |

TABLE 2

| Solvent | Relative Drop in component gc area count (%) | | | | |
|---|---|---|---|---|---|
|  | 134a | 134 | 1122 | 124 | 114x |
| Trichloroethylene | 0 | 9 | 66 | 51 | 69 |
| Tetrachloroethylene | 0 | 12 | 67 | 50 | 71 |
| Carbon tetrachloride | 0 | 12 | 68 | 54 | 74 |

TABLE 2-continued

| Solvent | Relative Drop in component gc area count (%) | | | | |
|---|---|---|---|---|---|
| | 134a | 134 | 1122 | 124 | 114x |
| Hexane | 0 | 6 | 63 | 52 | 75 |
| Cyclohexane | 0 | 5 | 65 | 46 | 75 |
| α-Pinene | 0 | 0 | 61 | 44 | 67 |
| COMPARISON | | | | | |
| 1,1,1-Trichloroethane | 0 | 13 | 60 | 54 | — |
| Pentachloroethane | 0 | 10 | 63 | 44 | 60 |
| Chloroform | 0 | 15 | 62 | 49 | — |
| 1,1,2-trichloro-1,2,2-trifluoroethane | 0 | 5 | 53 | 52 | — |
| Toluene | 0 | 25 | 57 | 58 | — |
| Ethanol | 0 | 41 | 36 | 68 | 22 |
| Methanol | 0 | 47 | 18 | 61 | (−16) |
| Water | 0 | 5 | (−2) | (−3) | — |
| Triethylamine | 0 | 34 | 66 | 78 | 68 |
| Perfluorohexane | 0 | 1 | 26 | 43 | 60 |

EXAMPLE 3

Three glass sample vials (volume 90 ml) were prepared and fitted with septa for gas addition and sampling. Each vial was evacuated then filled to 1 atmosphere pressure with a previously prepared gas mixture of 134a containing ca 1000 ppm by volume each of 134, 1122, 124 and 114x. A vapour sample (10 ml) was withdrawn from the sample vials and analysed by gc to obtain the initial gc area count for each component. The chosen extraction agent (10 ml) was then added to the vial and the contents were stirred for 1 hour at room temperature. A vapour sample (10 ml) was withdrawn, brought to atmospheric pressure by air addition, then analysed by gc to indicate the final gc area count for each component.

Table 3 lists the absolute drop in each component which occurred after exposure to the extraction agent (taken as an average of three runs). Table 4 shows the drop in components 134, 1122, 124 and 114x relative to that for 134a. This data is produced by normalising on the 134a i.e. the 134a initial level is divided by 134a final level to produce a ratio with which all the final component levels are multiplied such that the 134a initial level divided by the normalised 134a final level equals 1.

TABLE 3

| Solvent | Absolute Drop in component gc area count (%) | | | | |
|---|---|---|---|---|---|
| | 134a | 134 | 1122 | 124 | 114x |
| Trichloroethylene | 37.8 | 41.4 | 77.2 | 67.5 | 76.4 |
| Tetrachloroethylene | 36.6 | 53.3 | 77.5 | 67.0 | 78.3 |
| Carbon tetrachloride | 42.6 | 49.0 | 80.1 | 71.8 | 88.0 |
| Hexane | 40.3 | 42.4 | 77.8 | 70.7 | — |
| Cyclohexane | 32.5 | 30.9 | 74.0 | 62.8 | 82.5 |
| α-Pinene | 39.2 | 42.6 | 75.6 | 68.6 | 79.1 |
| COMPARISON | | | | | |
| 1,1,1-Trichloroethane | 62.5 | 66.7 | 82.0 | 79.3 | — |
| Pentachloroethane | 43.6 | 49.2 | 78.0 | 67.2 | — |
| Chloroform | 56.3 | 61.3 | 79.3 | 73.1 | — |
| 1,1,2-trichloro-1,2,2-trifluoroethane | 55.4 | 58.2 | 79.3 | 77.4 | — |
| Paraffin | 17.5 | 17.9 | 55.0 | 38.0 | — |
| Toluene | 66.1 | 75.9 | 85.9 | 86.2 | — |
| Water | 4.0 | 10.3 | 4.8 | 2.9 | — |

TABLE 4

| Solvent | Relative Drop in component gc area count (%) | | | | |
|---|---|---|---|---|---|
| | 134a | 134 | 1122 | 124 | 114x |
| Trichloroethylene | 0 | 9 | 58 | 45 | 61 |
| Tetrachloroethylene | 0 | 8 | 65 | 48 | 68 |
| Carbon tetrachloride | 0 | 11 | 64 | 49 | 74 |
| Hexane | 0 | 3 | 63 | 51 | — |
| Cyclohexane | 0 | 4 | 64 | 48 | 76 |
| α-Pinene | 0 | 7 | 60 | 49 | 66 |
| COMPARISON | | | | | |
| 1,1,1-Trichloroethane | 0 | 11 | 52 | 45 | — |
| Pentachloroethane | 0 | 10 | 61 | 42 | — |
| Chloroform | 0 | 14 | 53 | 37 | — |
| 1,1,2-trichloro-1,2,2-trifluoroethane | 0 | 4 | 49 | 45 | — |
| Paraffin | 0 | 0 | 45 | 25 | — |
| Toluene | 0 | 28 | 58 | 59 | — |
| Water | 0 | 6 | 1 | (+1) | — |

We claim:

1. A method for separating 1,1,1,2-tetrafluoroethane from a mixture containing 1,1,1,2-tetrafluoroethane and chlorine-containing halogenated hydrocarbons which comprises adding an extraction agent to said mixture, extractively distilling the mixture in an extractive distillation zone and recovering 1,1,1,2-tetrafluoroethane from the extractive distillation zone, the extraction agent being selected from trichloroethylene, perchloroethylene, carbon tetrachloride and aliphatic hydrocarbons containing from 4 to 10 carbon atoms.

2. A method as claimed in claim 1 wherein the extraction agent is trichloroethylene.

3. A method as claimed in claim 1 wherein the extraction agent is perchloroethylene.

4. A method as claimed in claim 1 wherein the extraction agent is hexane or cyclohexane.

5. A method as claimed in claim 1 wherein the extraction agent is alpha-pinene.

6. A method as claimed in any one of the preceding claims which comprises feeding the mixture of 1,1,1,2-tetrafluoroethane and chlorine-containing halogenated hydrocarbons to be separated to the centre of a fractionating column, feeding the extraction agent to the upper part of the column and removing from the column an overheads fraction comprising 1,1,1,2-tetrafluoroethane containing less than 10 ppm by weight of chlorine-containing halogenated hydrocarbons and a bottoms fraction comprising the extraction agent and chlorine-containing halogenated hydrocarbons separated from the 1,1,1,2-tetrafluoroethane.

7. A method as claimed in claim 6 wherein the fractionating column is operated at a pressure of from 1 to 15 bars.

8. A method as claimed in claim 1 wherein the extraction agent is a chlorinated hydrocarbon and after use the extraction agent containing one or more extracted species is fed as feedstock to a fluorination reactor.

9. A method as claimed in claim 8 wherein the extraction agent is trichloroethylene and the reaction performed in the fluorination reactor is the preparation of HFA 134a and/or an intermediate for use in the production of HFA 134a.

10. A method as claimed in claim 8 wherein the extraction agent is perchloroethylene and the reaction performed in the fluorination reactor is the preparation of 1,1-dichloro-2,2,2-trifluoroethane (HCFC 123), 1-chloro-1,2,2,2-tetrafluoroethane (HCFC 124) and/or pentafluoroethane (HFA 125).

* * * * *